(12) United States Patent
Irge

(10) Patent No.: US 8,608,786 B2
(45) Date of Patent: Dec. 17, 2013

(54) APPARATUS FOR DELIVERING MULTIPLE FORMS OF ELECTROMAGNETIC RADIATION AND METHOD FOR ITS USE

(76) Inventor: Dror Irge, Raanana (IL)

( * ) Notice: Subject to any disclaimer, the term of this patent is extended or adjusted under 35 U.S.C. 154(b) by 29 days.

(21) Appl. No.: 12/884,475

(22) Filed: Sep. 17, 2010

(65) Prior Publication Data

US 2011/0071602 A1 Mar. 24, 2011

Related U.S. Application Data

(60) Provisional application No. 61/243,696, filed on Sep. 18, 2009, provisional application No. 61/316,701, filed on Mar. 23, 2010.

(51) Int. Cl.
*A61N 5/067* (2006.01)
(52) U.S. Cl.
USPC .................... 607/88; 607/89; 607/90; 607/91
(58) Field of Classification Search
USPC ..................................... 606/2–19; 607/88–94
See application file for complete search history.

(56) References Cited

U.S. PATENT DOCUMENTS

| | | | |
|---|---|---|---|
| 4,945,541 A | 7/1990 | Nakayama | |
| 5,065,456 A | 11/1991 | Nakayama | |
| 5,280,536 A | 1/1994 | Dumond et al. | |
| 5,640,978 A | 6/1997 | Wong | |
| 6,157,661 A | 12/2000 | Walker et al. | |
| 6,267,779 B1 * | 7/2001 | Gerdes | 607/89 |
| 6,411,421 B1 | 6/2002 | Murai | |
| 2004/0030370 A1 | 2/2004 | Lytle | |
| 2004/0153131 A1 * | 8/2004 | Yorke | 607/91 |
| 2005/0004631 A1 | 1/2005 | Benedict | |
| 2005/0085875 A1 | 4/2005 | Van Zuylen | |
| 2007/0167999 A1 | 7/2007 | Breden et al. | |
| 2007/0260297 A1 | 11/2007 | Chariff | |

FOREIGN PATENT DOCUMENTS

| | | |
|---|---|---|
| WO | WO 2007/050144 A1 | 5/2007 |
| WO | WO 2009/023968 A1 | 2/2009 |

OTHER PUBLICATIONS

International Search Report and Written Opinion for PCT/IL2010/000771 dated Jan. 17, 2011.
Hashmi et al., Effect of Pulsing in Low-Level Light Therapy, 2010, pp. 450-466, vol. 46, Issue 6, Lasers in Surgery and Medicine.
Chow et al., Efficacy of Low-Level Laser Therapy in the Management of Neck Pain: A Systematic Review and Meta-Analysis of Randomised Placebo or Active-Treatment Controlled Trials, Dec. 5, 2009, pp. 1897-1908, vol. 374, The Lancet.

(Continued)

*Primary Examiner* — Aaron Roane
(74) *Attorney, Agent, or Firm* — Alston & Bird LLP

(57) ABSTRACT

An apparatus for delivering multiple forms of electromagnetic radiation and methods for its use are disclosed. An example embodiment may comprise a radiation unit having one or more light emitting diodes that emit electromagnetic radiation in continuous wave form and one or more laser diodes that emit electromagnetic radiation in continuous wave form. The radiation unit may be connected to a frequency generator that provides a waveform. The waveform may convert the continuous wave output of the laser diodes to pulse wave output, while leaving the continuous wave output of the light emitting diodes unaffected. The frequency generator may cause the emission of an additional electromagnetic field proximate the radiation unit. Associated apparatuses and methods for their use are also provided.

18 Claims, 3 Drawing Sheets

(56) References Cited

OTHER PUBLICATIONS

Streeter et al., Mechanisms of Action of Light Therapy for Stroke and Acute Myocardial Infarction, 2004, pp. 569-576, Mitochondrion.
Tuby et al., Low-Level Laser Irradiation (LLLI) Promotes Proliferation of Mesenchymal and Cardiac Stem Cells in Culture, 2007, pp. 373-378, Lasers in Surgery and Medicine.
Oron, Photoengineering of Tissue Repair in Skeletal and Cardiac Muscles, 2006, pp. 111-120, vol. 24, No. 2, Photomedicine and Laser Surgery.
Tuby et al., Modulations of VEGF and iNOS in the Rat Heart by Low Level Laser Therapy are Associated With Cardioprotection and Enhanced Angiogenesis, 2006, pp. 682-688, Lasers in Surgery and Medicine.
Yaakobi et al., Long-Term Effects of Low Energy Laser Irradiation on Infarction and Reperfusion Injury in the Rat Heart, 2001, pp. 2411-2419, J Appl Physiol.
Oron et al., Low-Energy Laser Irradiation Reduces Formation of Scar Tissue After Myocardial Infarction in Rats and Dogs, Jan. 16, 2001, pp. 296-301, Circulation.
Yousefi-Nooraie et al., Low Level Laser Therapy for Nonspecific Low-Back Pain (Review), 2008, 35 pages total, The Cochrane Collaboration.
Ad et al., Impact of Low Level Laser Irradiation on Infarct Size in the Rat Following Myocardial Infarction, 2001, pp. 109-116, International Journal of Cardiology.
Campana et al., Laser Therapy on Arthritis Induced by Urate Crystals, 2004, pp. 499-503, vol. 22, No. 6, Photomedicine and Laser Surgery.
Banzer et al., Laser-Needle Therapy for Spontaneous Osteonecrosis of the Knee, 2008, pp. 299-304, vol. 26, No. 4, Photomedicine and Laser Surgery.
Bjordal et al., A Systematic Review With Procedural Assessments and Meta-Analysis of Low Level Laser Therapy in Lateral Elbow Tendinopathy (Tennis Elbow), May 29, 2008, 15 pages total, BMC Musculoskeletal Disorders.
Brosseau et al., Low Level Laser Therapy for Osteoarthritis and Rheumatoid Arthritis: A Metaanalysis, Aug. 2000, pp. 1961-1969, The Journal of Rheumatology.
Shupak et al., Exposure to a Specific Pulsed Low-Frequency Magnetic Field: A Double-Blind Placebo-Controlled Study of Effects on Pain Ratings in Rheumatoid Arthritis and Fibromyalgia Patients, 2006, pp. 85-90, vol. 11, No. 2, Pain Res Manage.
Bjordal et al., A Systematic Review of Low Level Laser Therapy With Location-Specific Doses for Pain From Chronic Joint Disorders, Journal, 2003, pp. 107-116, vol. 49, Australian Journal of Physiotherapy.
Balogh, Transcutaneous Application of Pulsed Radiofrequency: Four Case Reports, Case Report, 2004, pp. 310-313, vol. 4, Issue 4, World Institute of Pain.
Rozen et al., Pulsed Radiofrequency for the Treatment of Ilioinguinal Neuralgia After Inguinal Herniorrhaphy, Journal, Jul. 2006, pp. 716-718, vol. 73, No. 4, The Mount Sinai Journal of Medicine.
Schofferman et al., Effectiveness of Repeated Radiofrequency Neurotomy for Lumbar Facet Pain, 2004, pp. 2471-2473, vol. 29, No. 21, Spine.
Husted et al., Effectiveness of Repeated Radiofrequency Neurotomy for Cervical Facet Joint Pain, Aug. 2008, pp. 406-408, vol. 21, No. 6, J Spinal Discord Tech.
Sadick et al., Nonablative Wrinkle Treatment of the Face and Neck Using a Combined Diode Laser and Radiofrequency Technology, Dec. 2005, pp. 1695-1699, American Society for Dermatologic Surgery, Inc.
Enwemeka et al., The Efficacy of Low-Power Lasers in Tissue Repair and Pain Control: A Meta-Analysis Study, 2004, pp. 323-329, vol. 22, No. 4, Photomedicine and Laser Surgery.
Gao et al., Molecular Mechanisms of Cell Proliferation Induced by Low Power Laser Irradiation, Journal, Jan. 12, 2009, 16 pages, Journal of Biomedical Science.
Thamsborg et al., Treatment of Knee Osteoarthritis with Pulsed Electromagnetic Fields: A Randomized, Double-Blind, Placebo-Controlled Study, Jul. 2005, 7 Pages Total, Osteoarthritis and Cartilage.
Sutbeyaz et al., The Effect of Pulsed Electromagnetic Fields in the Treatment of Cervical Osteoarthritis: A Randomized, Double-Blind, Sham-Controlled Trial, Jun. 29, 2005, 5 pages total, Rheumatol Int.
Kumar et al., Optimization of Pulsed Electromagnetic Field Therapy for Management of Arthritis in Rats, May 10, 2005, pp. 431-439, Bioelectromagnetics.
Ciombor et al., Modification of Osteoarthritis by Pulsed Electromagnetic Field—A Morphological Study, Jun. 2003, pp. 455-462, OsteoArthritis and Cartilage.

\* cited by examiner

APPARATUS FOR DELIVERING MULTIPLE FORMS OF ELECTROMAGNETIC RADIATION AND METHOD FOR ITS USE

CROSS-REFERENCE TO RELATED APPLICATIONS

This application claims priority to U.S. provisional application entitled, "Apparatus and method for pain relief and treatment of non-specific inflammation using low power laser in continuous wave form, pulse wave and electromagnetic field, simultaneously and separately" having Ser. No. 61/243,696, filed Sep. 18, 2009, and U.S. provisional application entitled, "Apparatus and method for pain relief and treatment of non-specific inflammation of smooth and skeletal muscle using low power laser in continuous wave form, pulse wave and electromagnetic field, simultaneously and separately" having Ser. No. 61/316,701, filed Mar. 23, 2010, both of which are entirely incorporated herein by reference.

FIELD OF THE INVENTION

The present invention is generally directed to an apparatus for delivering multiple forms of electromagnetic radiation, and methods for using the apparatus.

BACKGROUND

A light emitting diode, or LED, is formed from a semiconducting material having a p-n junction. The p-n junction creates an electric field that separates charge carriers, namely free electrons and holes. When an electron reaches a hole, the two recombine and release energy in the process which generates a photon. The photon generally has a specific wavelength based on the band gap energy of the materials used to form the p-n junction. In particular, the materials used to form an LED have a direct band gap that corresponds to electromagnetic energies near the visible spectrum.

Other techniques may be used to cause the emission of electromagnetic radiation. One such technique is known as light amplification by stimulated emission of radiation, or a laser. Typically, the electromagnetic radiation emitted from a laser is in the form of photons of light energy that are monochromatic, meaning they have the same wavelength. The photons are also generally coherent and travel in a very tight beam toward the same direction.

One specific type of laser is known as a laser diode. A laser diode is a type of laser formed from a semiconductor much like an LED. Laser diodes differ, however, in that they employ an optical cavity that confines the emitted light into a very narrow line like a laser and may employ lenses to form a collimated beam. Thus, unlike LEDs, laser diodes exhibit the same properties described above that define a laser.

Laser diodes and LEDs may be used for treating patients in various fields of medicine including dermatology, dentistry, ophthalmology, gastroenterology, urology, gynecology, orthopedics, etc. The current methods for employing laser diodes and LEDs in treating patients in these fields, however, suffer from various drawbacks. Some techniques use very low frequencies that may be too low to be optimally effective in treatment. Other techniques require significantly higher frequencies to be effective, which may be dangerous and uncomfortable for patients due to the higher operating temperatures and additional heat that is emitted.

Many electromagnetic radiation therapy devices are too limiting, allowing the production of radiation output of only a single type, frequency, wavelength, etc. Furthermore, the devices allow only a static form of treatment, meaning that the selected type, frequency, wavelength, etc., of the radiation device may not be adjusted, added, or removed during operation of the device for treatment. Due to the various drawbacks of these devices, a patient generally will require recurring treatments as the derived benefit only lasts for a short duration of time.

Therefore, there is a strong need in the art for producing a radiation device for treating patients using laser diodes and LEDs that overcomes the above-mentioned and other disadvantages and deficiencies of previous technologies.

BRIEF SUMMARY OF SOME EXAMPLES OF THE INVENTION

Various embodiments of an apparatus for delivering multiple forms of electromagnetic radiation are herein disclosed. These embodiments of the invention overcome one or more of the above-described disadvantages associated with previous technologies. Embodiments of the invention provide several advantages for production of a radiation device that improves treatment and limits the cost required for its production.

According to an example embodiment of the invention, an apparatus for providing treatment using electromagnetic radiation therapy is provided. The apparatus comprises one or more light emitting diodes configured to provide for the emission of electromagnetic radiation in continuous wave form. The apparatus further comprises one or more laser diodes configured to provide for the emission of electromagnetic radiation in continuous wave form. Additionally, the apparatus comprises a frequency generator configured to provide a frequency generator waveform at a frequency. The frequency generator waveform converts the electromagnetic radiation of the one or more laser diodes from continuous wave form to pulse wave form and maintains the electromagnetic radiation of the one or more light emitting diodes in continuous wave form. Additionally, the frequency generator is further configured to cause the emission of an electromagnetic field proximate the apparatus.

According to another example embodiment of the invention, a method is disclosed for providing treatment using electromagnetic radiation therapy. The method comprises receiving a power input initiating a radiation unit. The radiation unit comprises one or more light emitting diodes, one or more laser diodes, and a frequency generator. The method further comprises initiating the one or more light emitting diodes to provide for the emission of electromagnetic radiation in continuous wave form. Additionally, the method comprises initiating the one or more laser diodes to provide for the emission of electromagnetic radiation in continuous wave form. The method further comprises controlling the frequency generator to provide a frequency generator waveform at a frequency to convert the output of the one or more laser diodes from continuous wave form to pulse wave form, maintain the output of the one or more light emitting diodes in continuous wave form, and cause the emission of an electromagnetic field proximate the radiation unit.

Another example embodiment of the invention is directed to a method for providing radiation treatment. The method comprises providing continuous wave electromagnetic radiation of a first wavelength. Additionally, the method comprises providing pulse wave electromagnetic radiation of a second wavelength. The method further comprises providing an electromagnetic field of a third wavelength. The first, second, and third wavelengths are different from one another. The continuous wave electromagnetic radiation, the pulse wave electromagnetic radiation, and the electromagnetic field are provided simultaneously by a single device.

The above summary is provided merely for purposes of summarizing some example embodiments of the invention so as to provide a basic understanding of some aspects of the invention. Accordingly, it will be appreciated that the above described example embodiments should not be construed to narrow the scope or spirit of the invention in any way more restrictive than as defined by the specification and appended claims. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

DETAILED DESCRIPTION

Figure 1:
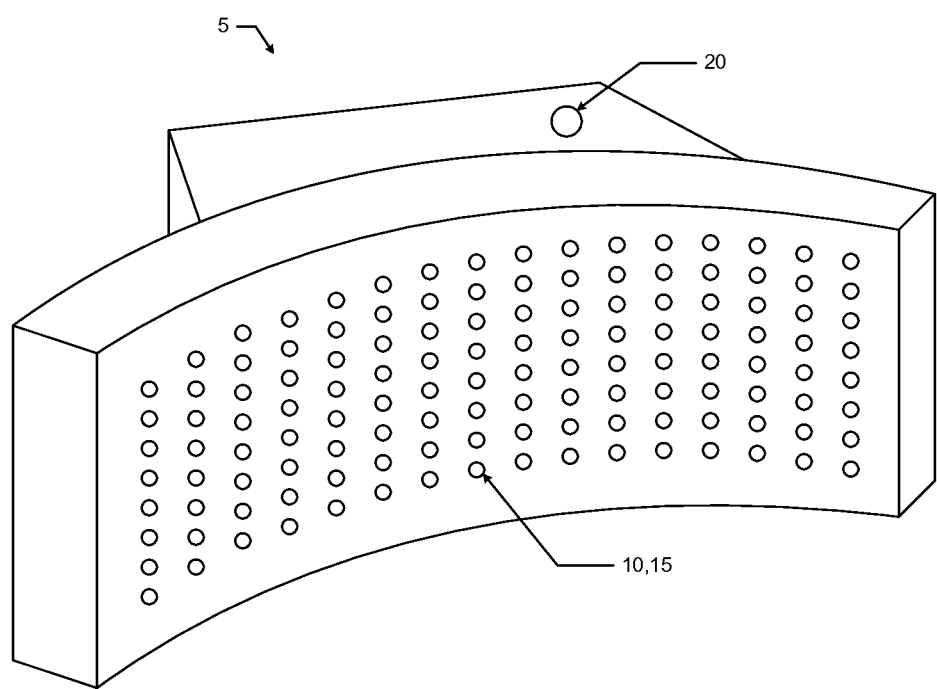
FIG. 1 illustrates a radiation apparatus in accordance with an example embodiment of the present invention.

Some embodiments of the present invention will now be described more fully hereinafter with reference to the accompanying drawings, in which some, but not all embodiments of the invention are shown. Those skilled in this art will understand that the invention may be embodied in many different forms and should not be construed as limited to the embodiments set forth herein; rather, these embodiments are provided so that this disclosure will satisfy applicable legal requirements. Like reference numerals refer to like elements throughout.

The radiation apparatus 5 according to the present invention may provide laser therapy through the combination of multiple types of electromagnetic radiation in a single device. The radiation apparatus 5 may allow a user to determine the desired combination among laser energy and other types of electromagnetic energy according to a patient's level of pain in addition to the level of inflammation. In certain embodiments, a user may be able to raise or lower the frequency of the radiation output according to the level of pain experienced by the patient alone. According to embodiments of the present invention, the type, form, frequency, and amount of radiation output may be adjusted during the operation of the radiation apparatus 5, without any side effects and at very low cost.

Within the application of treating pain and inflammation, the present invention may further be directed to treating cardiac cells affected by cardiac injury, for instance for treating a patient who suffers a myocardial infarction. Treatments based on the combination of various forms of electromagnetic radiation as in the present radiation apparatus 5 may decrease the infarct size, ventricular dilation post-myocardial infarction, and the size of the septum, among other things. Furthermore, similar treatment using the present invention may be provided to other types of muscle, skeletal and soft tissue as well as smooth muscle, which may assist in treatment of colitis, colitis ulcerosa, Crohn's disease, inflammation of the jejunum, and other chronic diseases.

FIG. 1 illustrates one embodiment of a radiation apparatus 5 in accordance with the present invention. The radiation apparatus 5 may comprise elements that emit light radiation energy. According to various embodiments, the light emitting elements may include one or more light emitting diodes (LEDs) 10. The LEDs 10 may be selected based on the wavelength of the light they emit. In some embodiments, each LED 10 may emit the same or approximately the same wavelength of radiation as the other LEDs 10. Alternatively, one or more LEDs 10 may emit radiation of a different wavelength than one or more other LEDs 10. In fact, any number of different types of LEDs 10 emitting different wavelengths of radiation may be used in combination in the same radiation apparatus.

The selection of an LED 10 of a given wavelength may be based on the form of treatment desired to be achieved by the radiation apparatus. According to example embodiments, the LEDs 10 may be selected such that the central wavelength of the emitted light is within the range of 635 to 650 nm, for example 650 nm. In such example embodiments, the LEDs 10 may emit radiation in the form of visible light, in particular red light. It should be understood that the present invention is not limited to LEDs 10 emitting radiation of this wavelength and may include LEDs 10 that emit radiation at any wavelength, including radiation of other wavelengths within the visible spectrum, infrared spectrum, ultraviolet spectrum, and beyond.

According to various embodiments, the light emitting elements may comprise one or more laser diodes 15. The laser diode elements 15 may be chosen based on the wavelength of the light they emit. In some embodiments, each laser diode 15 may emit the same or approximately the same wavelength of radiation as the other laser diodes 15. Alternatively, one or more laser diodes 15 may emit radiation of a different wavelength than one or more other laser diodes 15. In fact, any number of different types of laser diodes 15 emitting different wavelengths of radiation may be used in combination in the same radiation apparatus.

The selection of a laser diode 15 of a given wavelength may be based on the form of treatment desired to be achieved by the radiation apparatus. According to example embodiments, the laser diodes 15 may be selected such that the central wavelength of the emitted light is within the range of 780 to 785 nm, for example 785 nm. In such example embodiments, the laser diodes 15 may emit radiation in the form of infrared radiation, which is invisible to the human eye. It should be understood that the present invention is not limited to laser diodes 15 emitting radiation of this wavelength and may include laser diodes 15 that emit radiation at any wavelength, including radiation of other wavelengths within the infrared spectrum, visible spectrum, ultraviolet spectrum, and beyond.

According to an example embodiment, the radiation apparatus 5 comprises a combination of one or more LED 10 elements and one or more laser diode 15 elements. In alternative embodiments, the radiation apparatus may comprise only laser diodes 15. The LEDs 10 and laser diodes 15 may be arranged in a matrix layout. The number of LEDs 10 and laser diodes 15 in the radiation unit may be varied to achieve a particular treatment objective. In an example embodiment, the radiation unit may comprise 64 LEDs 10 and 64 laser diodes 15. Although these embodiments employ the same number of LEDs 10 and laser diodes 15, alternatively, the number of LEDs 10 may differ from the number of laser diodes 15. The LEDs 10 and laser diodes 15 may be arranged in the matrix in a number of rows and columns, for example 16 rows and 8 columns. An example embodiment of a base laser radiation unit that may be modified according to the present invention is the Hyper Photon 3D from Medical Electronics GmbH. It is appreciated that various other types of base laser radiation units may be modified according to the present invention.

According to some embodiments, the LEDs 10 and laser diodes 15 may be disposed along the inside of a curved surface of the radiation apparatus 5, for example a surface that approximates a lateral half of a cylinder. In some embodiments, each LED 10 and laser diode 15 may be positioned such that the radiation from the element emits toward the axis of the cylinder. The LEDs 10 and laser diodes 15 may be spaced evenly along the curve. In example embodiments, the distance between the centers of two adjacent elements may be approximately 20 mm. The length of the arc of a row of elements may be 290 mm and have a sagittal distance of 90 mm. According to these example embodiments, the curvature radius of a row may be approximately 160 mm. As illustrated in FIG. 1, each radiation element may be either a light emitting diode 10 or a laser diode 15.

Figure 2:
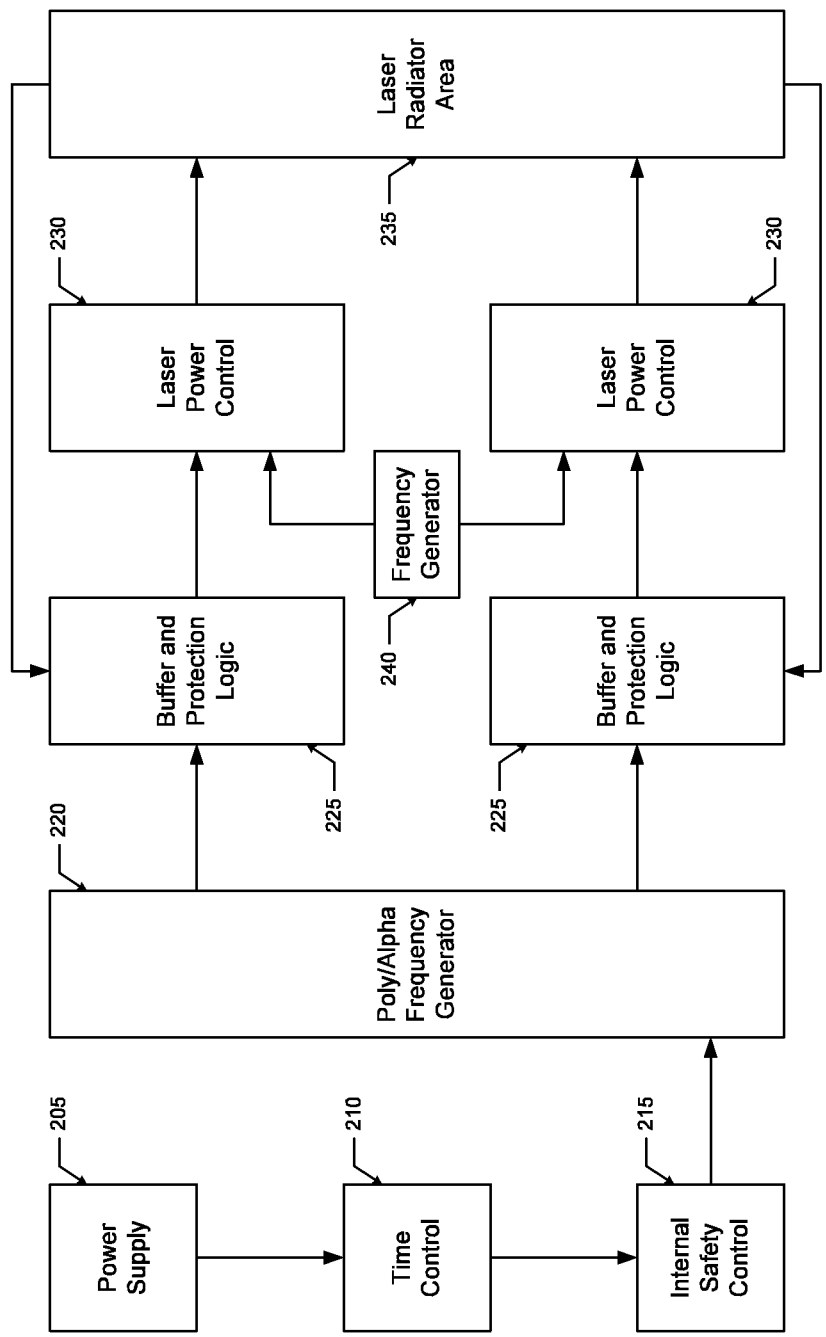
FIG. 2 illustrates a schematic representation of a radiation apparatus in accordance with an example embodiment of the present invention.

In certain embodiments, the radiation apparatus 5 may further include additional elements for controlling the radiation emitting elements, as shown in the schematic representation of FIG. 2. The radiation apparatus 5 may comprise for example, a power supply element 205, a time control element 210, an internal safety control element 215, a poly/alpha frequency generator element 220, one or more buffer and protection logic elements 225, one or more laser power control elements 230, a laser radiator area element 235, and/or the like. Although not shown, the radiation apparatus 5 may also include various other components for controlling and powering the radiation apparatus 5 and its radiation elements, for example a processing device (e.g., a processor, controller, and/or the like). It will be appreciated that one or more of these radiation apparatus 5 components may be located remotely from one another. Furthermore, one or more of the components may be combined and additional components performing functions described herein may be included.

According to example embodiments, the radiation apparatus 5 may further comprise a frequency generator 240, or modulator. The frequency generator 240 may be used to generate an electrical waveform as an input to the radiation apparatus 5. According to certain embodiments, the frequency generator 240 may be external to the radiation apparatus 5. The external frequency generator 240 may be any commercially available frequency generator 240 that can be connected or disconnected based on the type of treatment to be applied. An example of such an external frequency generator 240 is model MXG 9802 manufactured by Voltcraft (Lindenweg 15, D-92242 Hirschau/Germany). In embodiments with an external frequency generator 240, an output of the frequency generator 240 may be connected to an input of the radiation apparatus 5, for example via an optional input jack 20. The optional input jack 20 of the radiation apparatus 5 may be a type of pin connector commonly used in electrical instruments that accepts inputs in the form of a plug. According to alternative embodiments, the frequency generator 240 may be a component internal to the radiation apparatus 5 and connected to one or more of the other internal components of the radiation apparatus 5.

According to certain embodiments, a user of the radiation apparatus 5 may be able to control the output waveform of the frequency generator 240. In particular, the frequency generator 240 may have an accessible control that allows a user to increase or decrease the frequency of the output waveform during the operation of the radiation apparatus 5. Additionally, in certain embodiments, the frequency generator 240 may have a toggle control such that the frequency generator 240 may be initiated or terminated during the operation of the radiation apparatus 5. In these embodiments, the frequency generator 240 may be alternatively initiated and terminated as many times as desired during the operation of the radiation apparatus 5.

Figure 3:
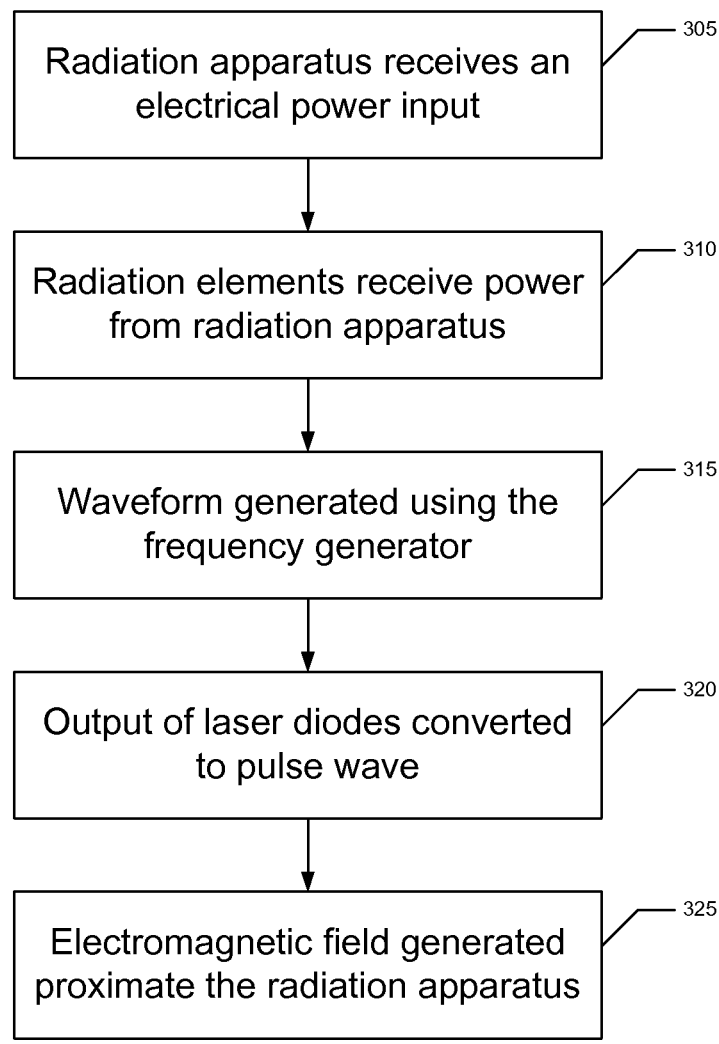
FIG. 3 illustrates a flowchart according to an example embodiment of a method for using a radiation apparatus of the present invention.

FIG. 3 illustrates a flowchart according to an example method for using the radiation apparatus 5 according to an example embodiment of the present invention. Other embodiments of the present invention may use different steps or different variations of the radiation apparatus 5. Accordingly, the described example of FIG. 3 is provided for illustrative purposes only and should not be taken in any way as limiting embodiments of the present invention to the example provided.

Referring to FIG. 3, according to one embodiment, at operation 305 a radiation apparatus may receive an electrical power input. The power input may be provided by an external voltage source such as a standard wall socket supplying mains power, for example an alternating current (AC) voltage source in the range of 110 to 250 volts at a frequency of 50-60 hertz (Hz). Alternatively, the power supply may be an internal power supply that allows the radiation apparatus 5 to benefit from added mobility.

At operation 310, the components of the radiation apparatus 5 may provide power to the radiation elements 10, 15 of the radiation apparatus 5. In certain embodiments, the LED elements 10 may be configured to receive power sufficient to produce a continuous wave radiation output at a power density of approximately 1 milliwatt per centimeter squared ($mW/cm^2$). The laser diode elements 15 may be configured to receive power sufficient to produce a continuous wave radiation output at a power density of approximately 6 $mW/cm^2$. According to various embodiments of the present invention, the intensity of radiation for either the LED elements 10 or laser diode elements 15 may range from approximately 1 $mW/cm^2$ to approximately 55 $mW/cm^2$.

Operation 315 may comprise generating a waveform at a particular frequency using the frequency generator 240. The waveform of the frequency generator 240 may be applied to the radiation elements 10, 15 of the radiation apparatus 5. According to an example embodiment, the frequency generator 240 may apply the waveform to the radiation elements 10, 15 via the one or more laser power control elements 230. Alternatively, the waveform of the frequency generator 240 may be applied to the laser diodes 15 but not the LEDs 10. It will be appreciated that the waveform from the frequency generator 240 may be applied to the radiation elements 10, 15 via various other components of the radiation apparatus 5.

At operation 320, the continuous wave output of the laser diodes 15 may be converted to pulse wave output due at least in part to the waveform applied by the frequency generator 240. According to various embodiments, the frequency of the pulse wave of the laser diode 15 radiation output may equal or approximate the frequency of the waveform supplied by the frequency generator 240. As a result, the frequency of the pulse wave of the laser diodes 15 may be controlled by modifying the frequency of the waveform supplied by the frequency generator 240. That is, the pulse rate of the laser diodes 15 may correspond closely or identically with the frequency of the waveform of the frequency generator 240.

The output waveform of the frequency generator 240 may have any frequency desired, which may depend on the type of treatment to be provided by the radiation apparatus 5. In certain embodiments, the output waveform of the frequency generator 240 may range from 0.1 hertz to over 2.5 megahertz (MHz). The frequency of the waveform of the frequency generator 240, and therefore the frequency of the pulse wave output of the laser diodes 15, may be increased without compromising the integrity of the pulse wave output of the laser diodes 15. Additionally, it may be possible to obtain pulses with variable repetition rates and pulse widths by controlling the frequency and shape of the modulating waveform of the frequency generator 240 as well as its duty cycle. By changing the laser diodes 15 output from continuous wave to pulse wave and adjusting its frequency, the radiation apparatus 5 may provide enhanced pain relief without any relation or dependence on the wavelength of the radiation output.

By using the method of the present invention, no additional components aside from the frequency generator 240 are required to convert the continuous wave output of the laser diodes 15 to pulse wave output. In particular, the conversion of the continuous wave output of the laser diodes 15 to pulse wave output may be achieved without the use of a pulse generator inside a laser tube. That is, there is no need to bombard the laser diodes 15 with different types of radiation to achieve the conversion, but rather the user need only modulate the continuous wave output of the laser diodes 15. As a result, the amount of energy delivered to the patient is not increased, as the output is simply modulated. Thus, the present invention provides the advantages of simplicity, control, and reduced cost in comparison to the alternatives.

At operation 325, an electromagnetic field may be generated in close proximity to the radiation apparatus 5. The electromagnetic field may form as a result of enabling the frequency generator 240. In some embodiments, the electromagnetic field may be in the form of RF radiation, that is, radiation having a frequency in the range of 9 kilohertz (kHz) to 300 gigahertz (GHz). According to example embodiments, the intensity of the electromagnetic radiation may vary depending on the modulating frequency of the frequency generator 240.

In an example embodiment, the detectable intensity of the electromagnetic field proximate the radiation apparatus 5 when the frequency generator 240 is disabled may be approximately 0.3 volts per meter (V/m). In this example embodiment, when the frequency generator 240 is enabled at a relatively low modulating frequency in the range of approximately 0.1 to 0.2 MHz, the intensity of the electromagnetic field may be approximately 0.72 V/m. In this same example embodiment, when the frequency generator 240 is enabled at a relatively high modulating frequency in the range of approximately 1 to 2.5 MHz, the intensity of the electromagnetic field may be approximately 1.73 V/m. Thus, the intensity of the electromagnetic field may increase at relatively higher modulating frequencies by approximately 250% more than at relatively lower modulating frequencies.

An unexpected result of the present invention is the fact that the continuous wave output of the LED elements 10 is not affected by the waveform of the frequency generator 240. In certain embodiments, the frequency generator 240 may be enabled thereby both converting the continuous wave output of the laser diodes 15 to pulse wave output and generating an electromagnetic field without affecting the continuous wave output of the LED elements 10. As a result, the radiation apparatus 5 may simultaneously provide pulse wave laser diode output, continuous wave LED output, and an electromagnetic field output in a single device when the frequency generator 240 is enabled.

As noted above, the frequency generator 240 may be enabled or disabled during operation of the radiation apparatus 5 as desired in order to switch the output of the laser diodes 15 back and forth between pulse wave and continuous wave. Additionally, the frequency generator 240 may be enabled or disabled during operation of the radiation apparatus 5 to increase or decrease the intensity of the electromagnetic field generated proximate the radiation apparatus 5. Similarly, the modulating frequency of the frequency generator 240 may be increased or decreased during operation of the radiation apparatus 5 as desired in order to increase or decrease the pulse rate of the output pulse wave of the laser diodes 15. The modulating frequency of the frequency generator 240 may also be increased or decreased during operation of the radiation apparatus 5 as desired in order to increase or decrease the intensity of the electromagnetic field generated proximate the radiation apparatus 5. Accordingly, the output levels of the radiation apparatus 5 can be adjusted, namely via the frequency generator 240, thus enabling the radiation apparatus 5 to switch the laser diodes 15 outputs between continuous wave and pulse wave, and to increase and decrease the electromagnetic field proximate the radiation apparatus 5 without the need for building separate devices. Additionally, the wavelengths of the radiation outputs of the LEDs 10 and the laser diodes 15 outputs may be adjusted for treatment of different pain or inflammation conditions.

The use of the example embodiment of the radiation apparatus 5 according to the example method provided, as well as additional embodiments of the radiation apparatus 5 and additional methods for using the radiation apparatus 5, may be useful in the field of laser therapy. In particular, the radiation apparatus 5 may be useful in the general treatment of both pain and inflammation in a patient. According to certain embodiments, the continuous wave output of the LEDs 10 may provide anti-inflammation relief. The continuous wave output of the laser diodes 15 may provide analgesic relief. The pulse wave output of the laser diodes 15 may similarly provide analgesic relief. In some instances the pulse wave output of the laser diodes 15 provides greater analgesic relief than the continuous wave output of the laser diodes 15. Like the outputs of the laser diodes 15, the electromagnetic field generated proximate the radiation apparatus 5 may also provide pain relief.

The radiation apparatus 5 according to the present invention is also directed to methods of treating pain generally. In several example embodiments, the present invention includes methods of treating orthopedic pain, neurological pain, rheumatic pain, muscle pain, tendon pain, joint pain, nerve pain, as well as pain and inflammation of smooth, skeletal, and cardiac muscle, including cardiac pain and myocardial infarction (MI). In some embodiments, treatment of the smooth muscle may assist with treatment of colitis, colitis ulcerosa, Crohn's disease, inflammation of the jejunum, and other chronic diseases. Use of the frequency generator in the present invention will allow for a patient's pain relief to be varied over time.

In example embodiments, the radiation apparatus 5 may be positioned proximate the treatment area of the patient during operation. In particular, the radiation apparatus 5 may be positioned from one to ten inches from the treatment area of the patient. According to alternative embodiments, the radiation apparatus 5 may be pressed directly against the patient's skin, covering an area of approximately 20 cm×10 cm in front of the treatment area.

According to various embodiments, the combination of the three types of radiation outputs may provide additional benefits over their separate use. In particular, the combination of the electromagnetic field with the laser diodes may improve pain treatments of a patient. The radiation output of the laser diodes 15 may lower the impedance of the target area on a patient, in some embodiments by warming the target area, so that the RF radiation from the electromagnetic field may penetrate more deeply and more easily into the target area.

Such improved penetration may allow the RF radiation to reach the soft tissue of the patient at the target area thereby increasing the intensity of the effect on the patient. In particular, the more penetrating radiation outputs may provide significantly improved treatment on the peripheral nervous system, including the sympathetic system.

Pain alleviation may be felt by the patient when the modulating frequency of the frequency generator 240 is approximately 20 kHz and when the corresponding electromagnetic field intensity is 0.72 V/m. Generally, beyond this intensity, pain relief may be mainly due to the RF field, which is still weak enough not to produce erythema on skin. In additional embodiments of the present invention, the laser diodes 15 may achieve pain relief when the modulating frequency is at least 10 kHz. It is appreciated, however, that the present invention is not limited to a certain frequency range of the pulse wave laser diodes 15.

According to example embodiments, the radiation apparatus 5 according to the present invention may achieve pain relief by applying a modulating frequency of approximately 1 to 2 MHz such that the pulse wave output of the laser diodes 15 achieves the same frequency pulse rate. Alternatives to the present invention are less favorable due to the use of low level laser therapy, which is typically limited to noninvasive treatments up to 10 kHz. The present invention, however, may provide significantly higher frequencies of radiation output that will further reduce pain beyond the capacity of devices limited to 10 kHz.

Additionally, the operation of the present invention according to the design of the radiation apparatus 5 does not produce the expected negative effects due to the higher frequencies used in the embodiment described above. For example, unlike certain cosmetic devices used in dermatological clinics that are limited to a single radiation output at very high frequencies of 4 to 8 MHz, the present invention does not produce additional heat or elevated temperatures that can be damaging to the patient. The lack of additional heat output at the higher frequency output may be a result of the ability of the present invention to modulate the radiation outputs at higher frequencies without the need to increase the overall energy of the radiation apparatus 5. Moreover, the use of the present invention does not require invasive techniques such as the injection of needles into the patient parallel to the target nerve at high temperatures, as practiced with RF treatments in pain clinics.

As noted above, an additional benefit in the treatment of patients with radiation apparatus 5 of the present invention is the ability to simultaneously provide anti-inflammation and analgesic relief with a single device. Due to the fact that the radiation outputs of the LEDs 10 are not affected by the modulating waveform of the frequency generator 240, the single radiation apparatus 5 of the present invention may provide the anti-inflammatory benefits of the LEDs 10 along with the pain-relieving benefits of the laser diodes 15 and the electromagnetic field. Of additional significance is the fact that the radiation output of the LEDs 10 does not affect the ability of the frequency generator 240 to modulate the pulse wave output of the laser diodes 15 at a given frequency or to increase the intensity of the electromagnetic field.

Through the use of the various forms of electromagnetic radiation outputs at different wavelengths, the radiation apparatus 5 of the present invention may help achieve significant, if not complete, resolution of pain resulting from cardiac injury, such as a myocardial infarction. The present invention may be useful not only for treatment of patients with high risk of cardiac injury, but also, in certain embodiments, the present invention may be used to treat persons suffering from definite cardiac injury.

The use of the radiation apparatus 5 to provide laser therapy to patients suffering from or at risk of cardiac injury may enhance ATP synthesis, mitochondrial survival and maintenance of cytochrome C oxidase activity, accelerate wound healing, promote skeletal muscle regeneration, decrease inflammatory response, reduce infarct size, reduce the size of the septum, reduce release of troponin, reduce scar tissue, reduce ventricular dilatation, up-regulate key factors that regulate angiogenesis and cardioprotection in the ischemic heart (vascular endothelial growth factor (VEGF) and inducible nitric oxide synthase (iNOS)), elevate inducible heat shock protein (HSP70i), increase presence of loose matrix containing sparse collagen post MI, and induce proliferation of existing cardiac stem cells (CSCs), among other things.

The present invention provides the additional benefit that it does not require the chest cavity to be open, or the skin removed to the side, to provide treatment to patients with cardiac injury. That is, the present invention may treat a myocardial infarction and its effects without undertaking any invasive procedures. Instead, the radiation apparatus 5 may be positioned closely above the patient's chest directed toward the patient's heart. In one example embodiment the radiation apparatus 5 may be placed very close to the patient's chest. In another preferred embodiment, the radiation apparatus 5 may be pressed directly against the patient's skin, covering an area of approximately 20 cm×10 cm in front of the heart. As a result of the combined effect of the various forms of electromagnetic radiation along with the ability to change the wave mode of the laser diodes 15 (i.e., from continuous to pulse and back), the present invention may achieve penetration of the heart muscle.

The administration of the radiation apparatus 5 treatment to the heart may be made either before a patient's diagnosis of a myocardial infarction, after the diagnosis, or both before and after diagnosis. In several example embodiments, the radiation apparatus 5 of the present invention may be used to treat a patient suffering from symptoms related to a myocardial infarction. In these embodiments, the use of the radiation apparatus 5 may achieve reduction in the size of the ischemic area of the patient's heart, reduction in any necrotic area of the patient's heart, reduction in dilation of the left ventricle, and reduction in the size of the septum. In another example embodiment, the radiation apparatus 5 of the present invention may reduce the septum to normal size.

Treatment with the radiation apparatus 5 may reduce blood viscosity for a limited period of time, thereby increasing oxidation and increasing blood supply to the heart. Such treatment according to the present invention may be used before, during, and after diagnosis of acute myocardial infarction to achieve significant health benefits. Additional benefits may be accomplished by using the radiation apparatus 5 in combination with blood diluting medication, such as, for example, heparin.

The operation of the radiation apparatus 5 of the present invention is simple and reliable. It can easily be operated by any doctor, nurse, or technician seeking to treat a patient with several conditions generally involving pain and inflammation. The present radiation apparatus 5 may allow for improved treatment of pain and inflammation at lower cost because, as previously mentioned, it operates without inputting more energy than is required for a laser device that solely operates in continuous mode. Moreover, the radiation apparatus 5 may be embodied as a single device that does not require the use of expensive techniques to form a pulse wave from the continuous wave output of the laser diodes 15.

In an additional embodiment of the present invention, a computer, processor, controller, or the like may be connected to the radiation apparatus 5 to establish the proper treatment energy level in joules for the particular medical syndrome to be treated. According to various embodiments, the radiation apparatus 5 and the above treatment may be administrated in addition to the conventional treatment.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of steps, elements, and/or materials than those explicitly described above are also contemplated as may be set forth in some of the appended claims. Accordingly, the specification and drawings are to be regarded in an illustrative rather than restrictive sense. Although specific terms are employed herein, they are used in a generic and descriptive sense only and not for purposes of limitation.

The invention claimed is:

1. An apparatus for providing treatment using electromagnetic radiation therapy, said apparatus comprising:
    a plurality of light emitting diodes configured to provide for the emission of electromagnetic radiation in continuous wave form and at a first wavelength during operation of said apparatus;
    a plurality of laser diodes configured to provide for the emission of electromagnetic radiation in continuous wave form and at a second wavelength during operation of said apparatus;
    a frequency generator configured to provide a frequency generator waveform at a frequency, wherein:
        the frequency generator waveform, during operation of said apparatus, simultaneously (1) converts the electromagnetic radiation of the plurality of laser diodes from continuous wave form to pulse wave form; and (2) maintains the electromagnetic radiation of the plurality of light emitting diodes in continuous wave form;
        the frequency generator is further configured to emit an electromagnetic field at a third wavelength and proximate the apparatus during operation of said apparatus; and
        the first, second, and third wavelengths are different wavelengths relative to one another and configured for simultaneous emission during operation of said apparatus.

2. The apparatus of claim 1, wherein the frequency generator further comprises a frequency control configured to adjust the frequency of the frequency generator waveform.

3. The apparatus of claim 2, wherein the frequency control is configured to adjust the frequency of the frequency generator waveform one or more times during a single treatment with the apparatus.

4. The apparatus of claim 1, wherein the pulse rate of the electromagnetic radiation of the plurality of laser diodes is the same as the frequency of the frequency generator waveform.

5. The apparatus of claim 1, wherein the frequency generator further comprises a toggle control configured to:
    initiate the output of the frequency generator waveform; and
    terminate the output of the frequency generator waveform.

6. The apparatus of claim 5, wherein the toggle control initiates the output of the frequency generator waveform one or more times and terminates the output of the frequency generator waveform one or more times during a single treatment with the apparatus.

7. The apparatus of claim 1, wherein the first wavelength is in the visible light spectrum, the second wavelength is in the infrared light spectrum, and the third wavelength is in the radio spectrum so as to produce radio frequency radiation.

8. The apparatus of claim 1 further comprising:
    an input jack, wherein the frequency generator is external to the apparatus, and wherein the frequency generator is operably connected to the apparatus via the input jack.

9. The apparatus of claim 1 further comprising:
    a processor, wherein the processor is configured to establish the energy level of the apparatus based on the condition to be treated.

10. The apparatus of claim 1, wherein the pulse rate of the electromagnetic radiation of the plurality of laser diodes increases relative to a corresponding increase of a frequency of the frequency generator and vice versa.

11. An apparatus for providing treatment using electromagnetic radiation therapy, said apparatus comprising:
    a plurality of light emitting diodes configured to provide for the emission of electromagnetic radiation in continuous wave form;
    a plurality of laser diodes configured to provide for the emission of electromagnetic radiation in continuous wave form;
    a frequency generator configured to provide a frequency generator waveform at a frequency, wherein:
        the frequency generator waveform simultaneously (1) converts the electromagnetic radiation of the plurality of laser diodes from continuous wave form to pulse wave form; and (2) maintains the electromagnetic radiation of the plurality of light emitting diodes in continuous wave form; and
        the frequency generator is further configured to emit, proximate the apparatus, an adjustable electromagnetic field in pulse form and at a wavelength in the radio spectrum so as to produce radio frequency (RF) radiation.

12. The apparatus of claim 1, wherein:
    the apparatus further comprises a curved surface; and
    the plurality of light emitting diodes and the plurality of laser diodes are disposed across the curved surface.

13. The apparatus of claim 12, wherein the plurality of light emitting diodes and the plurality of laser diodes are disposed across the curved surface such that the radiation emitted thereby is directed toward an axis of the cylinder.

14. The apparatus of claim 12, wherein the plurality of light emitting diodes and the plurality of laser diodes are distributed evenly across the curved surface.

15. The apparatus of claim 11, wherein:
    the apparatus further comprises a curved surface; and
    the plurality of light emitting diodes and the plurality of laser diodes are disposed across the curved surface.

16. The apparatus of claim 15, wherein the plurality of light emitting diodes and the plurality of laser diodes are disposed across the curved surface such that the radiation emitted thereby is directed toward an axis of the cylinder.

17. The apparatus of claim 15, wherein the plurality of light emitting diodes and the plurality of laser diodes are distributed evenly across the curved surface.

18. An apparatus for providing treatment using electromagnetic radiation therapy, said apparatus comprising:
- a plurality of light emitting diodes configured to provide for the emission of electromagnetic radiation in continuous wave form and at a first wavelength during operation of said apparatus;
- a plurality of laser diodes configured to provide for the emission of electromagnetic radiation in continuous wave form and at a second wavelength during operation of said apparatus;
- a frequency generator configured to provide a frequency generator waveform at a frequency, wherein:
  - the frequency generator waveform, during operation of said apparatus, converts the electromagnetic radiation of the plurality of laser diodes from continuous wave form to pulse wave form having a frequency the same as the frequency of the frequency generator waveform;
  - the frequency generator waveform, during operation of said apparatus, maintains the electromagnetic radiation of the plurality of light emitting diodes in continuous wave form, wherein the maintaining of the continuous wave form of the electromagnetic radiation of the plurality of light emitting diodes occurs simultaneously with the conversion into pulse wave form of the electromagnetic radiation of the plurality of laser diodes;
  - the frequency generator is further configured to emit an electromagnetic field in pulse form at a third wavelength and proximate the apparatus during operation of said apparatus; and
  - the first, second, and third wavelengths are different wavelengths relative to one another and are configured for providing a simultaneous and adjustable emission during operation of said apparatus.

* * * * *